United States Patent [19]

Juergens, Jr.

[11] Patent Number: 4,619,662

[45] Date of Patent: Oct. 28, 1986

[54] INTRAOCULAR LENS

[76] Inventor: Albert M. Juergens, Jr., 45 Windsor Ct., Box 418, Norwood, N.J. 07648

[21] Appl. No.: 724,875

[22] Filed: Apr. 19, 1985

[51] Int. Cl.⁴ .............................................. A61F 2/16
[52] U.S. Cl. ...................................................... 623/6
[58] Field of Search .............................. 623/6, 4, 8, 11

[56] References Cited

U.S. PATENT DOCUMENTS

| | | | |
|---|---|---|---|
| 3,883,902 | 5/1975 | Lynch | 623/8 |
| 4,177,526 | 12/1979 | Kuppinger | 623/6 |
| 4,373,218 | 2/1983 | Schachar | 623/6 |
| 4,542,542 | 9/1985 | Wright | 623/6 |
| 4,562,600 | 1/1986 | Ginsberg et al. | 623/6 |

FOREIGN PATENT DOCUMENTS 2124500  2/1984  United Kingdom ................... 623/6

Primary Examiner—Ronald L. Frinks
Attorney, Agent, or Firm—Edward M. Fink

[57] ABSTRACT

An intraocular lens system including a soft bio-compatible elastomer lens is described. The lens is capable of being collapsed and inserted in the eye on the head of a cannula integral to the lens system.

1 Claim, 3 Drawing Figures

INTRAOCULAR LENS

BACKGROUND OF THE INVENTION

This invention relates to intraocular lenses. More particularly, the present invention relates to an intraocular lens system comprising a soft biocompatible elastomer lens.

During the past decade, the medical profession has made widespread use of intraocular lenses comprising polymethylmethacrylate, a hard plastic composition. Recently, workers in the art have utilized lenses comprising a soft bio-compatible silicone and studies have revealed that the use of these materials in combination yields a solid lens which may be inserted completely into the human eye in accordance with conventional surgical procedures.

In the implementation of such procedure, it is the desire of the operating surgeon to induce a minimum of trauma into the eye. However, the procedure involves the removal of the defective lens and the subsequent implantation of its replacement, an end result commonly attained by making an incision in the eye ranging from 8 to 11 millimeters in length which permits the surgeon access to the defective lens and its surrounding capsule.

Studies have continued over the years with a view toward reduction of the trauma induced in the eye by incision of the type described and recent advances in the field have attained this end by the use of phacoemulsion techniques. These techniques permit insertion of the new intraocular lens through an incision of as little as 3 millimeters. Unfortunately, this procedure is not compatible with the insertion of hard polymethylmethacrylate lenses and surgeons have found it necessary to increase the length of the incision to at least 8 millimeters again, so obviating the advantages of the phacoemulsion technology.

SUMMARY OF THE INVENTION

In accordance with the present invention, the foregoing limitations have been successfully obviated by the use of an intraocular lens system including a soft biocompatible elastomer lens capable of being collapsed and inserted into the eye on the head of a cannula integral to the lens system. The collapsed lens is then structured within the chamber of the eye into its operative shape by the injection therein of a predetermined amount of elastomer into the collapsed lens mantle through a needle connected to the cannula, thereby obviating the necessity for a large incision and the traumatic manipulation required by unfolding a solid silicone lens.

BRIEF DESCRIPTION OF THE DRAWING

The invention will be more fully understood by reference to the following detailed description taken in conjunction with the accompanying drawing wherein.

DETAILED DESCRIPTION

In accordance with the present invention, a posterior or anterior chamber intraocular lens together with a surgical procedure for implantation of the lens in a human eye is described.

Figure 1:
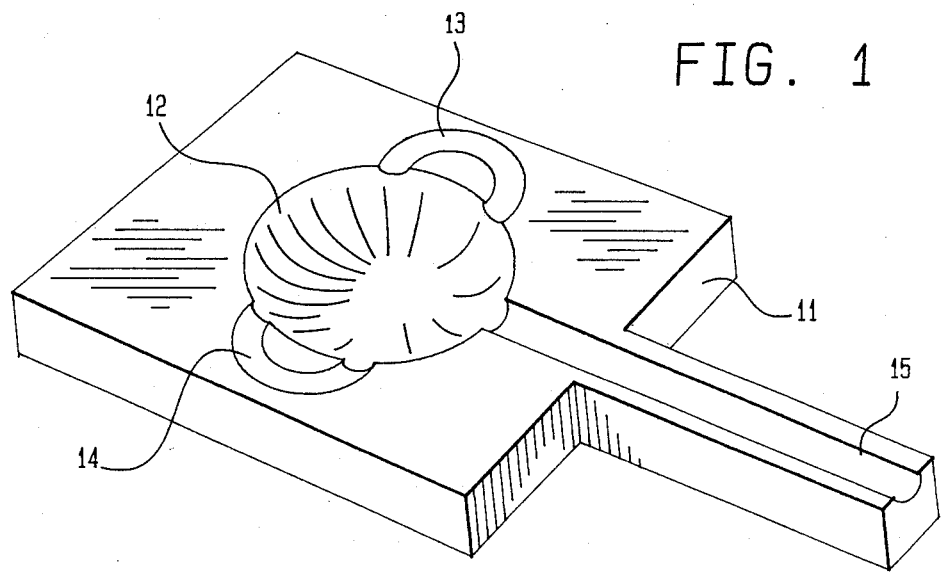
FIG. 1 is a plan view of a mold used in the preparation of an intraocular lens in accordance with the invention.

With reference now to FIG. 1, there is shown a plan view of half of a mold used in fabricating the intraocular lens described herein. Shown in the figure is mold 11 having disposed therein a cavity 12 to accommodate a lens, cavities 13 and 14 to accommodate haptics (optional) for the lens and cavity 15 to accommodate a cannula for the lens.

In the fabrication of the described lens, a polished mold 11.(FIG. 1) in the shape required for the correct refraction of light for the material selected is employed. The material chosen for this purpose is a bio-compatible elastomer obtained from commercial sources having known refractive power, silicone elastomers being found ideally suited for this purpose.

Figure 2:
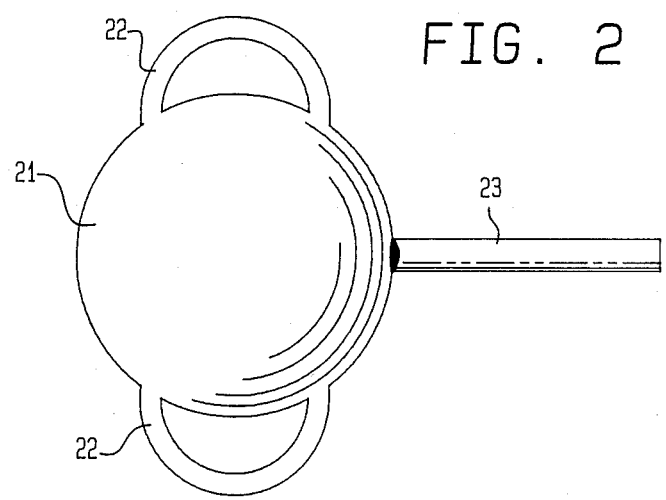
FIG. 2 is a front elevational view of an intraocular lens fabricated in accordance with the described procedure, the lens including a cannula and haptics.

Initially, the bio-compatible silicone elastomer of medical grade is injected into the lens cavity 12 of the mold of FIG. 1 through cannula 15, the amount of polymer introduced being dictated by considerations relating to lens size, refractive power and structure. Following, the mold is warmed at a temperature of the order of 150 degrees centigrade to cure the surface of the elastomer. Then, air is injected into the lens via the cannula to remove the silicone elastomer which remains uncured, the volume of air being based upon the volume of the lens and preferably not in excess of 70 percent of the volume of the lens. Next, the silicone elastomer is fully cured by further heating at temperature and duration appropriate to elastomer selected, and the lens removed from the mold. FIG. 2 is a front elevational view of the resultant lens showing lens mantle 21 comprised o the cured silicone elastomer. Haptics 22 serve as protrusions attached to the lens which hold it in place after implantation in the eye. Cannula 23 which is integral to lens mantle 21 serves as the mechanism by which the soft bio-compatible lens will be inserted into the eye. The structure of FIG. 2, of course, includes the air bubble inserted during the molding process and it will be appreciated that it is in this form that the lens structure will be shipped as an article of commerce.

Prior to surgical implantation, the air contained within the lens cavity of the structure shown in FIG. 2 is evacuated, so resulting in the collapse of the lens mantle on the tip of the cannula which bears the needle employed in the injection of the elastomer and introduction of air. The surgeon begins the operative procedure by making the required incision in the eye which is that warranted by the phacoemulsion technology, typically of the order of 3 millimeters in length. Then, the defective lens is removed and the collapsed lens of the required refractive power is inserted into the eye and appropriately positioned. At that juncture, a premeasured amount of silicone elastomer is injected into the collapsed cavity which had previously been formed by the air bubble, so resulting in the formation of a solid refracting lens in the shape of the original mold. The cannula, which is no longer required may then be incised from the lens by the use of a suitable laser cut made possible through the application of a laser selective dyestuff at the junction between the lens and the cannula. The lens insertion procedure is now completed and the surgeon may then suture the incision. It will be understood that the addition of the elastomer to the lens during the surgical procedure is rapid and does not interfere with the implementation of the surgical procedure. The elastomer will cure at body temperature after injection into the lens mantle.

Figure 3:
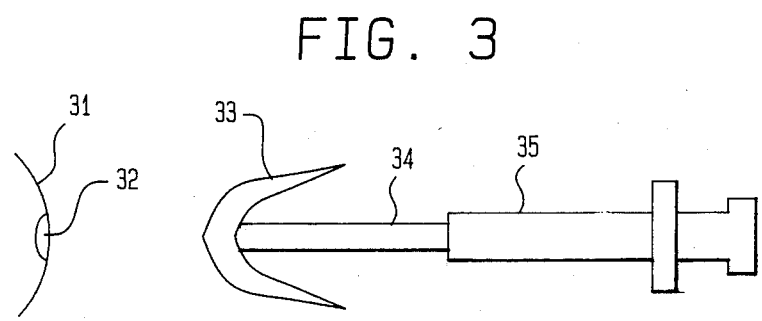
FIG. 3 is a side view of a human eye showing the lens of the invention in its collapsed state just prior to insertion in the eye.

FIG. 3 is a side view of the lens during the surgical implantation procedure. Shown in the figure is a human eye 31 having an incision 32 therein, collapsed lens and haptics 33, cannula 34 and syringe 35 used for injection of the elastomer into the lens mantle during the surgical procedure.

The lens described herein provides a simple, safe mechanism for restoration of a patient's vision by implantation of a soft intraocular lens which obviates the necessity of radial cutting of a cornea. The lens described has integral haptics which today represents the preferred method of attachment and positioning. The concept of the substitution of an entire lens within the lens capsule for a defective lens further simplifies the procedure.

It will be understood by those skilled in the art that the present invention has been described in terms of preferred embodiments. However, it will be appreciated that numerous modifications of the methodology are considered to be within the scope of the invention as defined by the appended claims.

What is claimed is:

1. Intraocular lens for an eye comprising a preformed molded mantle or lens having an accurately molded and polished exterior surface and a hollow interior of a first determined volume, said hollow interior being filled with a bio-compatible silicone elastomer having a predetermined volume equal to said first predetermined volume of the cavity whereby said lens assumes a predetermined refractory power.

* * * * *